(12) United States Patent
Toida

(10) Patent No.: US 7,557,931 B2
(45) Date of Patent: Jul. 7, 2009

(54) OPTICAL COHERENCE TOMOGRAPHY METHOD

(75) Inventor: Masahiro Toida, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 91 days.

(21) Appl. No.: 11/529,425

(22) Filed: Sep. 29, 2006

(65) Prior Publication Data

US 2007/0086011 A1 Apr. 19, 2007

(30) Foreign Application Priority Data

Sep. 30, 2005 (JP) .............................. 2005-288658

(51) Int. Cl.
*G01B 9/02* (2006.01)
(52) U.S. Cl. ..................................... 356/497
(58) Field of Classification Search .................. 356/479, 356/497

See application file for complete search history.

(56) References Cited

U.S. PATENT DOCUMENTS

2003/0076506 A1* 4/2003 Fercher ....................... 356/497

FOREIGN PATENT DOCUMENTS

JP 6-165784 A 6/1994

JP 2003-139688 A 5/2003

OTHER PUBLICATIONS

Yimin Wang, et al. "Ultrahigh-Resolution Optical Coherence Tomography by Broadband Continuum Generation From a Photonic Crystal Fiber" Optics Letters, vol. 28, No. 3, pp. 182-184, 2003.

* cited by examiner

*Primary Examiner*—Hwa S Lee (Andrew)
(74) *Attorney, Agent, or Firm*—Sughrue Mion, PLLC

(57) ABSTRACT

Low coherence light is divided into measuring light and reference light. The measuring light is collected to be projected onto an object of measurement. Intensities of the reflected light in a plurality of positions in the direction of depth are detected by carrying out a Fourier analysis on each channeled spectrum obtained by decomposing the detected interference light into frequency components. The optical path length of the reference light is stepwise changed to adjust the optical path length within the focusing range of the measuring light. A plurality of pieces of data representing the intensity of the reflected light are obtained in a plurality of positions in the direction of depth each time the position of the focusing range changes, and data on the position in the direction of depth where the measuring light is in the focusing range is extracted out of the pieces of data.

11 Claims, 6 Drawing Sheets

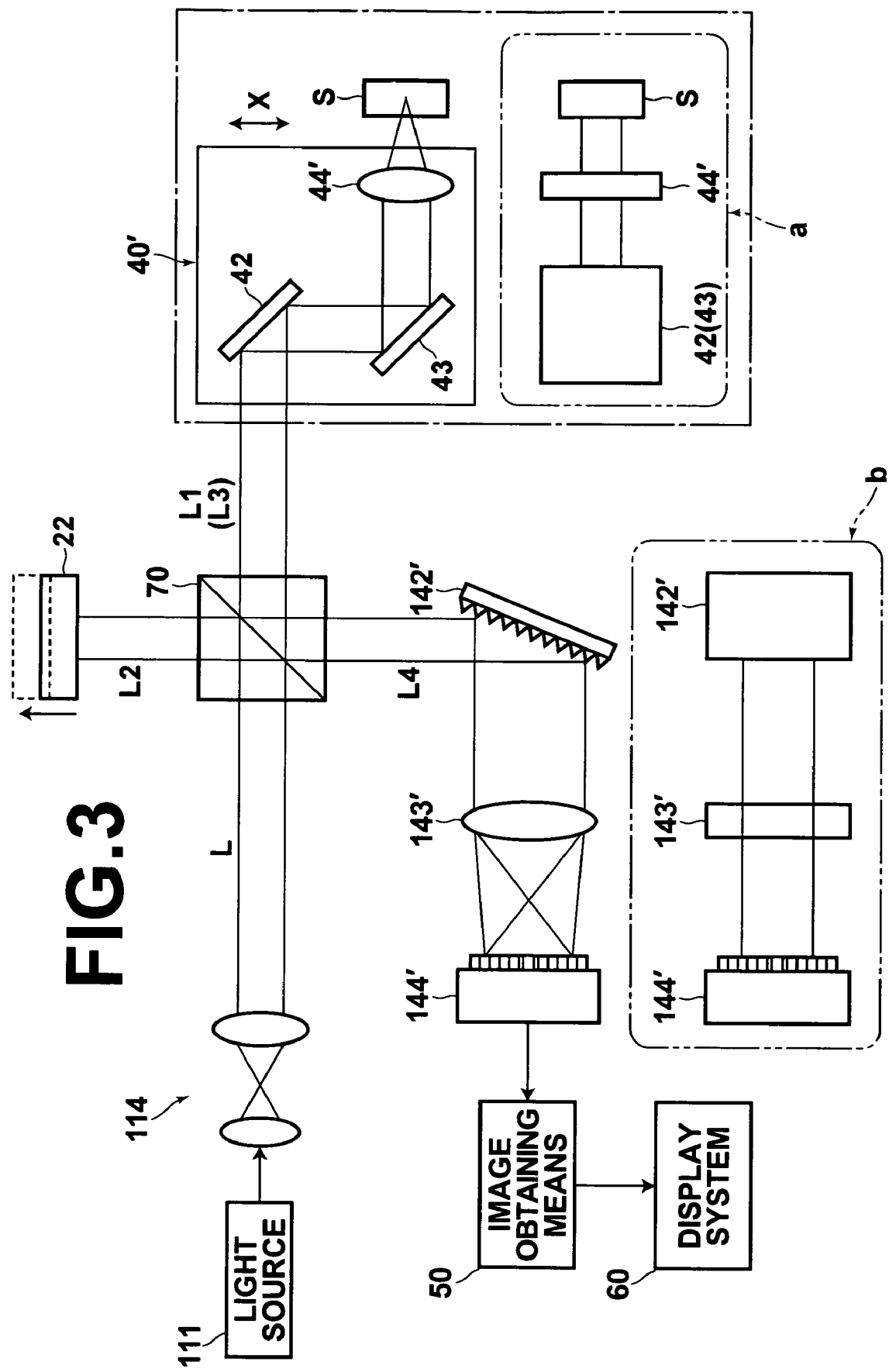

OPTICAL COHERENCE TOMOGRAPHY METHOD

BACKGROUND OF THE INVENTION

1. Field of the Invention

This invention relates to an optical tomography method of obtaining an optical tomographic image by measurement of OCT (optical coherence tomography), and more particularly to an optical tomography method of obtaining an optical tomographic image by measurement of SD-OCT (spectral domain OCT).

2. Description of the Related Art

As a method of obtaining a tomographic image of an object of measurement such as living tissue, it is proposed to measure OCT (optical coherence tomography) as disclosed in Japanese Unexamined Patent Publication Nos. 6(1994)-165784 and 2003-139688. In the OCT measurement, a phenomenon that interference light is detected when the optical paths of the measuring light and the reflected light conform to the optical path of the reference light in length is used. That is, in this method, low coherent light emitted from a light source is divided into measuring light and reference light and the measuring light is projected onto the object of measurement, while the reflected light from the object of measurement is led to a multiplexing means. The reference light is led to the multiplexing means after its optical path length is changed in order to change the depth of measurement in the object. By the multiplexing means, the reflected light and the reference light are superposed one on another, and interference light due to the superposition is detected by, for instance, heterodyne detection.

In the above OCT system, a tomographic image is obtained by changing the optical path length of the reference light, thereby changing the measuring position (the depth of measurement) in the object. This technique is generally referred to as "TD-OCT (time domain OCT)". More specifically, in the optical path length changing mechanism for the reference light disclosed in Japanese Unexamined Patent Publication No. 6(1994)-165784, an optical system which collects the reference light emitted from the optical fiber on a mirror is provided and the optical path length is adjusted by moving only the mirror in the direction of the beam axis of the reference light. Further, in the optical path length changing mechanism for the reference light disclosed in Japanese Unexamined Patent Publication No. 2003-139688, the reference light emitted from the optical fiber is turned to parallel light, the reference light in the parallel light is collected and caused to enter the optical fiber again by an optical path length adjusting lens, and the optical path length adjusting lens is moved back and forth in the direction of the beam axis of the reference light.

Whereas, as a system for rapidly obtaining a tomographic image without changing the optical path length of the reference light, there has been proposed an optical tomography system for obtaining an optical tomographic image by measurement of SD-OCT (spectral domain OCT). In the SD-OCT system, a tomographic image is formed without scanning in the direction of depth, by dividing broad band, low coherent light into measuring light and reference light by the use of a Michelson interferometer, projecting the measuring light onto the object and carrying out a Fourier analysis on each channeled spectrum obtained by decomposing the interference light of the reflected light, which returns at that time, and the reference light.

One of the characteristics of OCT is that the resolution in the direction of depth, that is, in the direction of the optical axis, is not limited by the NA (numerical aperture) of the optical system. That is, the resolution $\Delta z$ in the direction of the optical axis is defined by the following formula (1), wherein $\lambda$ and $\Delta\lambda$ respectively represent the central wavelength of the measuring light and the full width half maximum of the spectrum of the measuring light.

$$\Delta z = 2 \ln 2/\pi (\lambda^2/\Delta\lambda) \quad (1)$$

Accordingly, as shown in FIG. 4, even in a low NA optical system in which, for instance, $\lambda=1.3$ μm and $\Delta\lambda=35$ nm, a high resolution $\Delta z$ ($\Delta z=20$ nm) in the direction of the optical axis can be realized.

The beam diameter $\Delta x$ and the focal depth b of the measuring light beam in the converging position is defined by the following formulae (2) and (3), wherein the focal length and the diameter of the lens are respectively represented by f and d.

$$\Delta x = 4\lambda/\pi (f/d) \quad (2)$$

$$b = \pi \Delta x^2 / 2\lambda \quad (3)$$

FIG. 5 shows how the beam diameter changes with change of the position in the direction of the optical axis when the beam diameter $\Delta x$ of the measuring light beam in the converging position which governs the lateral resolution of the tomographic image takes various values. In FIG. 5, curves 1, 2, 3, 4, 5 and 6 respectively show the cases where $\Delta x=1$ μm, 3 μm, 10 μm, 20 μm, 30 μm and 100 μm. Further, the position 0 in the direction of the optical axis represents the converging position. As shown in FIG. 5, when, for instance, $\Delta x=20$ μm, the bean diameter hardly changes even in a position about 750 μm away from the converging position in the direction of the optical axis, whereby $\Delta x=20$ μm is substantially held with the focal depth b within the range of b=1.5 mm.

The OCT systems are frequently for taking a tomographic image of an area of about 3 mm (in the direction of the optical axis)×5 mm (laterally: in the direction perpendicular to the optical axis) and initially have been developed for use in the field of ophthalmology. FIG. 6 shows a representative example of the TD-OCT systems. The TD-OCT system 200 comprises: a light source unit 110 comprising a light source 111 for emitting a light beam L and a collecting lens 112; a light dividing means 2 for dividing the light beam L emitted from the light source unit 110 to be propagated through an optical fiber FB1; a light dividing means 3 for dividing the light beam L passing therethrough into a measuring light beam L1 and a reference light beam L2; an optical path length adjusting means 20 for adjusting the optical path length of the reference light beam L2 divided by the light dividing means 3 to be propagated through an optical fiber FB3; an optical probe 30 that irradiates the measuring light beam L1 divided by the light dividing means 3 to be propagated through an optical fiber FB2 onto an object S of measurement; a multiplexing means 4 (the dividing means 3 doubles) for multiplexing a reflected light beam L3, which is the measuring light beam L1 reflected from the object S, and the reference light beam L2; and an interference light detecting means 240 for detecting interference light beam L4 of the reflected light beam L3 and the reference light beam L2 which have been multiplexed by the multiplexing means 4.

The optical path length adjusting means 20 comprises a collimator lens 21 which makes parallel the reference light beam L2 radiated from the optical fiber FB3, a mirror 23 which is movable in the direction of arrow A to change the distance to the collimator lens 21, and a mirror moving means 24 which moves the mirror 23 and changes the optical path length of the reference light beam L2, thereby changing the measuring position in the object S in the direction of depth. Further, on the optical path of the reference light beam L2 (in the optical fiber FB3), a phase modulating means 210 which slightly shifts the frequency of the reference light beam L2 is disposed. The reference light beam L2 which has been changed in its optical path length and shifted with its frequency by the optical path length adjusting means 20 is led to the multiplexing means 4.

The interference light detecting means 240 detects the intensity of the interference light L4 propagating through the optical fiber FB2 from the multiplexing means 4, for instance, by heterodyne detection. Specifically, when the sum of the whole optical path length of the measuring light beam L1 and the whole optical path length of the reflected light beam L3 is equal to the whole optical path length of the reference light beam L2, a beat signal which varies in intensity at the difference frequency between the reference light beam L2 and the reflected light beam L3 is generated. As optical path length is changed by the optical path length adjusting means 20, the measuring position (depth) in the object S is changed, whereby the interference light detecting means 240 comes to detect a plurality of beat signals which are generated in a plurality of the measuring position in the object S. The information on the measuring position is output to the image obtaining means from the interference light detecting means 240. Then an optical tomographic image is generated on the basis of the beat signals detected by the interference light detecting means 240 and information on the measuring position in the mirror moving means 24.

In the conventional OCT system having such a structure, the movement of the mirror 23 in the direction of the optical axis and the lateral scanning of the measuring light beam L1 are generally carried out at about one fourth of a desired resolution when an optical tomographic image is to be obtained. That is, when a resolution of about $\Delta x=\Delta z=20$ μm, the mirror 23 is moved in the direction of the optical axis at pitches of about 5 μm, and the light beam is laterally scanned at pitches of about 5 μm.

At present, a high resolution, high sensitivity and high speed OCT system is developed attempting application to a field other than the field of ophthalmology. More specifically, it is desired a high resolution system where the present resolution of about $\Delta x=\Delta z=20$ μm is improved to not higher than 10 μm and it is desired a super high resolution system where the present resolution of about $\Delta x=\Delta z=20$ μm is improved to not higher than 5 μm.

When $\Delta x=\Delta z=10$ μm, it will be understood from FIG. 5 that the distance in the direction of the optical axis over which $\Delta x=10$ μm is held is about 200 μm. Similarly, when $\Delta x=\Delta z=5$ μm, it will be understood that the distance in the direction of the optical axis over which $\Delta x=5$ μm is held is about 50 μm. Accordingly, it cannot be avoided a problem that, when a tomographic image of an area longer than a length in the direction of the optical axis where a desired beam diameter range can be held is intended to be obtained while a desired lateral resolution is kept to be held, the lateral resolution deteriorates in the deeper or shallower region.

As a method of overcoming the problem, a method disclosed, for instance, in "Ultrahigh-Resolution Optical Coherence Tomography by Broadband Continuum Generation from a Photonic Crystal Fiber", Yimin Wang et al., OPTICS LETTERS, Vol. 28, No. 3, pp. 182-184, 2003, has been known. In this method, image data in the focusing position of the measuring light beam can be constantly obtained by changing the focusing position of the measuring light beam in synchronization with adjustment of the optical path length of the reference light beam and the method is called "dynamic focus OCT".

However, the above dynamic focus OCT involves a problem that a long time is required to collect image data necessary for forming a tomographic image since the scanning mechanism for the measuring light beam must be fed at fine pitches in the direction of the optical axis. If so, though a sample removed from a living tissue can be measured, in vivo measurement on a living body while it moves is impossible.

SUMMARY OF THE INVENTION

In view of the foregoing observations and description, the primary object of the present invention is to provide an optical tomography method which can hold high resolution and can collect image data at high speed in both the direction of the optical axis and the lateral direction.

An optical tomography method of the present invention is based on the SD-OCT measurement described above and in accordance with the present invention, there is provided an optical tomography method in which low coherence light emitted from a light source is divided into measuring light and reference light, the measuring light is collected by a lens system to be projected onto an object of measurement, the reflected light from the object and the reference light are multiplexed, interference light of the reflected light and reference light which have been multiplexed is detected, intensities of the reflected light in a plurality of positions in the direction of depth of the object of measurement are detected by carrying out a Fourier analysis on each channeled spectrum obtained by decomposing the detected interference light into frequency components and a tomographic image of the object is obtained on the basis of the intensity of the reflected light in each position in the direction of depth, wherein the improvement comprises the steps of stepwise changing the optical path length of the reference light thereby adjusting the optical path length of the reference light within the focusing range with respect to the object of the measuring light collected by the lens system, obtaining a plurality of pieces of data representing the intensity of the reflected light in a plurality of positions in the direction of depth each time the position of the focusing range changes, extracting data on the position in the direction of depth where the measuring light is in the focusing range out of the pieces of data representing the intensity of the reflected light, and obtaining a tomographic image on the basis of the extracted piece of data.

In the optical tomography method, it is especially preferred that stepwise changing the optical path length of the reference light be effected at pitches where the focusing range of the measuring light in the object changes by substantially the same extent as the focusing range of the measuring light.

The SD-OCT measurement is advantageous in that it can obtain a plurality of pieces of image data on a plurality of positions in the direction of the optical axis (direction of depth) at one time. Accordingly, when data representing the intensities of the reflected light from the object on a plurality of positions in the direction of the optical axis at one time and data on the position in the direction of depth where the measuring light is in the focusing range is extracted out of a plurality of pieces of the data representing the intensities of the reflected light as in the method in accordance with the present invention, a plurality of pieces of image data on a plurality of positions in the direction of the optical axis can be obtained at one time without feeding the scanning mechanism for the measuring light beam at pitches. Further, since such operation, while stepwise changing the optical path length of the reference light, is carried out each time the position of the focusing range of the measuring light changes, tomographic images of areas beyond the focusing range can be formed by joining a plurality of pieces of the data obtained by each operation.

When stepwise changing the optical path length of the reference light is effected at pitches where the focusing range of the measuring light in the object changes by substantially the same extent as the focusing range of the measuring light in the method of the present invention, a plurality of pieces of the data obtained by each operation are prevented from being unjustly joined with a lacking piece of data and at same time, the operation is prevented from being carried out at unnecessarily fine pitches, which is advantageous in rapidly forming a tomographic image.

BRIEF DESCRIPTION OF THE DRAWINGS

FIG. 3 is a schematic diagram showing an optical tomography system for carrying out an optical tomography method in accordance with a second embodiment of the present invention.

DESCRIPTION OF THE PREFERRED EMBODIMENTS

Figure 1:
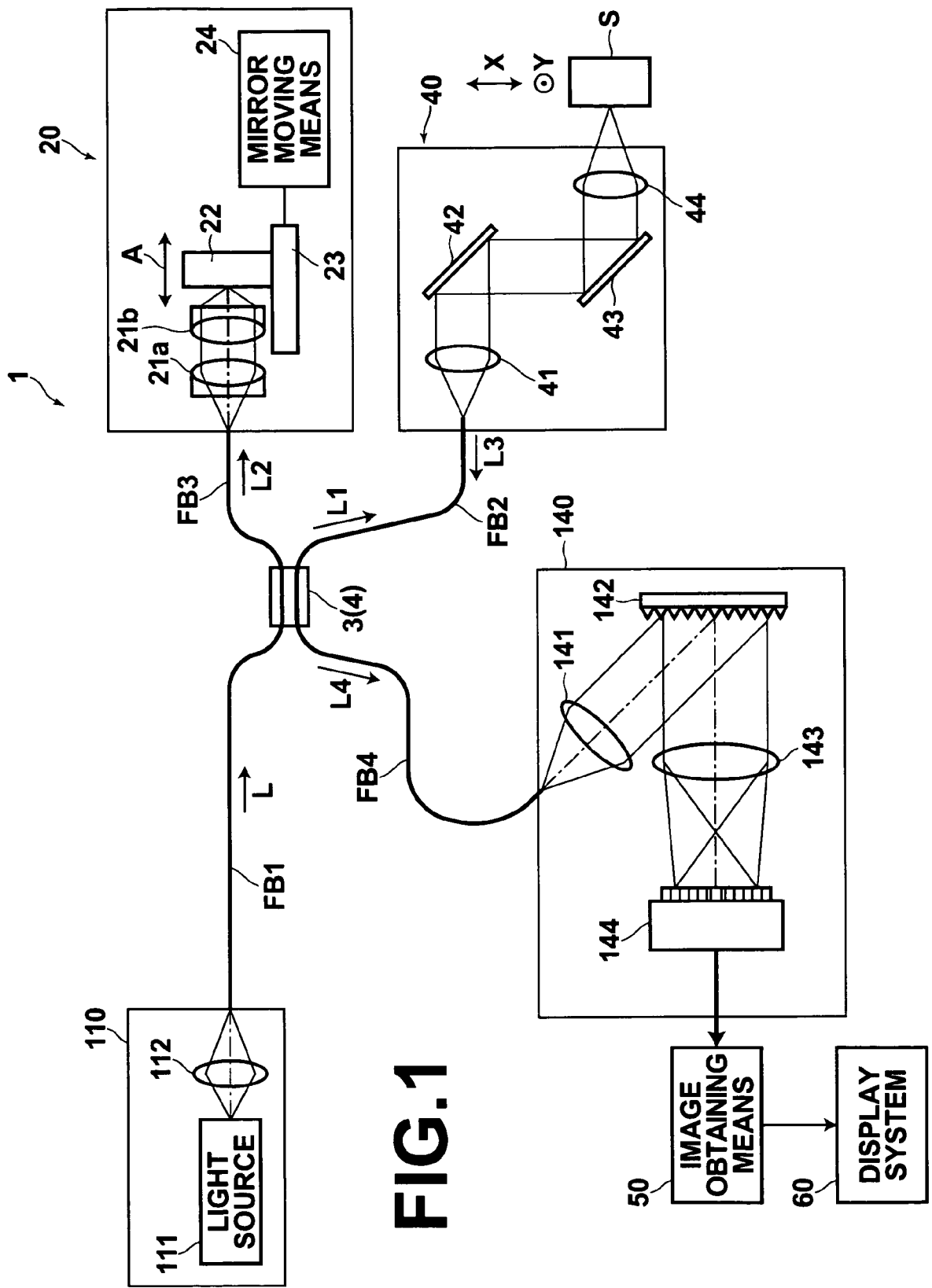
FIG. 1 is a schematic diagram showing an optical for carrying out an optical tomography method in accordance with a first embodiment of the present invention.

Embodiments of the present invention will be described in detail with reference to the drawings, hereinbelow. FIG. 1 is a schematic diagram that illustrates an optical tomography system in accordance with a first embodiment of the present invention. The optical tomography system 1 of this embodiment is for obtaining a tomographic image of an object of measurement such as a living tissue or a cell in a body cavity by measuring the SD-OCT. The optical tomography apparatus 1 of this embodiment comprises: a light source unit 110 for emitting a light beam L; a light dividing means 3 for dividing the light beam L emitted from the light source unit 110 into a measuring light beam L1 and a reference light beam L2; an optical path length adjusting means 20 for adjusting the optical path length of the reference light beam L2 divided by the light dividing means 3; a light scanning means 40 that irradiates the measuring light beam L1 divided by the light dividing means 3 onto the object S; a multiplexing means 4 for multiplexing a reflected light beam L3, which is reflected from the object S when the measuring light beam L1 is irradiated onto the object S, and the reference light beam L2; and an interference light detecting means 140 for detecting interference light beam L4 of the reflected light beam L3 and the reference light beam L2 which have been multiplexed.

The light source unit 110 comprises a light source 111 such as an SLD (super luminescent diode) or an ASE (amplified spontaneous emission) and an optical system 112 which causes the light beam emitted from the light source 111 to enter an optical fiber FB1. Since the optical tomography system 1 of this embodiment is for obtaining a tomographic image with a part of a living tissue in a body cavity taken as the object S, it is preferred that the light source 111 be, for instance, a broad spectral band, ultra short pulse laser where attenuation of light due to scatter and/or absorption when transmitted through the object S is minimized.

The light dividing means 3 comprises, for instance, a 2×2 fiber optic coupler and divides the light beam L led thereto by way of the optical fiber FB1 from the light source unit 110 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. In this embodiment, the light dividing means 3 also functions as the multiplexing means 4.

The light scanning means 40 is optically connected to the optical fiber FB2. The light scanning means 40 comprises a collimator lens 41 which makes parallel the reference light beam L2 radiated from the optical fiber FB2, a scanning mirror 42 which reflects the measuring light beam L1 emanating from the collimator lens 41, a scanning mirror 43 which reflects the measuring light beam L1 reflected by the scanning mirror 42 and a collecting lens 44 which collects the measuring light beam L1 reflected by the scanning mirror 43 to converge inside the object S.

The optical path length adjusting means 20 is disposed on the side of the optical fiber FB3 radiating the reference light beam L2. The optical path length adjusting means 20 changes the optical path length of the reference light beam L2 in order to adjust a position from which a tomographic image is initiated to be read out and comprises a reflecting mirror 22 which reflects the reference light beam L2 radiated from the optical fiber FB3, a first lens 21a disposed between the reflecting mirror 22 and the optical fiber FB3, and a second lens 21b disposed between the first lens 21a and the reflecting mirror 22.

The first lens 21a makes parallel the reference light beam L2 radiated from the core of the optical fiber FB3 and at the same time, collects the reference light beam L2 reflected by the reflecting mirror 2 on the core of the optical fiber FB3. The second lens 21b collects the reference light beam L2 made parallel by the first lens 21a on the reflecting mirror 22 and at the same time, makes parallel the reference light beam L2 reflected by the reflecting mirror 22. That is, the first and second lenses 21a and 21b form a confocal optical system.

Accordingly, the reference light beam L2 radiated from the optical fiber FB3 is turned to a parallel light by the first lens 21a and is collected on the reflecting mirror 22 by the second lens 21b. Subsequently, the reference light beam L2 reflected by the reflecting mirror 22 is turned to a parallel light by the second lens 21b and is collected on the core of the optical fiber FB3 by the first lens 21a.

The optical path length adjusting means 20 is further provided with a base 23 to which the second lens 21b and the reflecting mirror 22 are fixed and a mirror moving means 24 which moves the base 23 in the direction of the optical axis of the first lens 21a. In response to movement of the base 23 in the direction of arrow A, the optical path length of the reference light beam L2 can be changed.

The multiplexing means 4 shown in FIG. 1 comprises a 2×2 fiber optic coupler as described above, and multiplexes the reference light beam L2 which has been shifted in its frequency and changed in its optical path length by the optical path length adjusting means 20 and the reflected light beam L3 from the object S to emit the multiplexed light beam toward the interference light detecting means 140 by way of an optical fiber FB4.

The interference light detecting means 140 detects interference light L4 of the reflected light beam L3 and the reference light beam L2 which have been multiplexed by the multiplexing means 4, and comprises a collimator lens 141 which makes parallel the interference light beam L4 radiated from the optical fiber FB4, a spectral means 142 which divides the interference light beam L4 having a plurality of wavelength bands by the wavelength bands and a light detecting means 144 which detects each wavelength band of the interference light beam L4 divided by the spectral means 142.

The spectral means 142 comprises, for instance, a diffraction grating element, and divides the interference light beam L4 entering it to output the divided interference light beam L4 to the light detecting means 144. The light detecting means 144 is formed by, for instance, a CCD element which comprises a plurality of, for instance, one-dimensionally arranged photosensors and each of the photosensors detects each wavelength band of the interference light beam L4 divided as described above.

The light detecting means 144 is connected to an image obtaining means 50 which is connected to a display system formed, for instance, by a CRT or a liquid crystal display system. The light detecting means 144 is further connected to a storage means 70. The image obtaining means 50 and the storage means 70 comprises, for instance, a computer system such as a personal computer.

Operation of the optical tomography system 1 having a structure described above will be described, hereinbelow. For the purpose of simplicity, obtaining a general tomographic image where high resolution is not necessary will be described first. When a tomographic image is to be obtained, the optical path length is first adjusted by moving the base 23 in the direction of the arrow A so that the object S is positioned in the measurable area. The light beam L is emitted from the light source unit 110 and the light beam L is divided into the measuring light beam L1 and the reference light beam L2. The measuring light beam L1 is radiated from the light scanning means 40 toward a body cavity and is projected onto the object S. Then the reflected light beam L3 from the object S and the reference light beam L2 are multiplexed, and the interference light beam L4 of the reflected light beam L3 and the reference light beam L2 is detected. Information on the direction of depth of the object S is obtained by carrying out frequency analysis on the detected interference light beam L4 in the image obtaining means 50.

When the measuring light beam L1 is scanned X-direction and Y-direction perpendicular to the X-direction with respect to the object S, for instance, by moving in parallel the scanning mirrors 42 and 43 and the collecting lens 44 of the light scanning means 40, since information on the direction of depth of the object S is obtained at each part along the direction of this two-dimensional scan, tomographic images for both the X-direction and the Y-direction in this two-dimensional scanning area can be obtained.

When the base 23 is moved in the direction of the arrow A in order to adjust the optical path length (FIG. 1), the focus of the first lens 21a is never moved from the core of the optical fiber FB3. Further, the focus of the second lens 21b is never moved from the reflecting mirror 22. Accordingly, reduction of the amount of the reference light beam L2 when reentering the optical fiber FB3 after adjusted with its optical path length can be prevented, whereby deterioration of the image quality due to change of the intensity of the interference light beam L4 every time the optical path length is adjusted can be prevented.

In the light detecting means 144 of the interference light detecting means 140, the interference light beam L4 where Fourier-transformed function of information on the reflection is added to the spectrum of the measuring light beam L1 is observed. Accordingly, information on the direction of depth of the object S is obtained by carrying out in the image obtaining means 50 frequency analysis on the interference light beam L4 detected in the interference light detecting means 140.

The obtainment of the information on the direction of depth of the object Sb will be described in more detail. The wave motion of the reflection with respect to the wave motion $V^{(r)}_T(t)$ from the light source is expressed by the following formulae (4) and (5) when information on the reflection of the object S such as a living tissue is represented by $R(\tau)$.

$$V^{(r)}_T(t) \otimes R(t) \tag{4}$$

$$V^{(r)}_T(t) + V^{(r)}_T(t) \otimes R(t) \tag{5}$$

Accordingly, autocorrelation of interference light wave is expressed as follows.

$$\int_{-\infty}^{\infty} \{V^{(r)}\tau(t) + V^{(r)}\tau(t) \otimes R(t)\} \tag{6}$$

$$\{V^{(r)}\tau(t+\tau) + V^{(r)}\tau(t+\tau) \otimes R(t+\tau)\} dt =$$

$$\int_{-\infty}^{\infty} \{V^{(r)}\tau(t)V^{(r)}\tau(t+\tau)\} dt + \int_{-\infty}^{\infty} V^{(r)}\tau(t)V^{(r)}\tau(t+\tau) \otimes R(t)dt +$$

$$\int_{-\infty}^{\infty} V^{(r)}\tau(t)V^{(r)}\tau(t+\tau) \otimes R(t+\tau)dt +$$

$$\int_{-\infty}^{\infty} V^{(r)}\tau(t)V^{(r)}\tau(t+\tau) \otimes R(t)R(t+\tau)dt$$

Since the fourth term is negligible and the third term becomes an integration of a minus time by carrying out a substitution of $t+\tau \rightarrow t$ and actually 0, $$\int_{-\infty}^{\infty} \{V^{(r)}\tau(t) + V^{(r)}\tau(t) \otimes R(t)\}\{V^{(r)}\tau(t+\tau) + V^{(r)}\tau(t+\tau) \otimes R(t+\tau)\} dt = \tag{7}$$

$$\int_{-\infty}^{\infty} \{V^{(r)}\tau(t)V^{(r)}\tau(t+\tau)\} dt + \int_{-\infty}^{\infty} V^{(r)}\tau(t)V^{(r)}\tau(t+\tau) \otimes R(t)dt$$

When formula (7) is considered on the basis of time regions, a waveform obtained by carrying out convolutional integration on the autocorrelation of the light source itself and the information on the reflection of the object S convoluted with the autocorrelation function (coherence function) of the light source itself is observed.

Further, when considered on the basis of spectral regions, formula (7) is written in the form of Fourier transform as follows.

$$\int_{-\infty}^{\infty} \{V^{(r)}\tau(t)V^{(r)}\tau(t+\tau)\}dt + \int_{-\infty}^{\infty} V^{(r)}\tau(t)V^{(r)}\tau(t+\tau) \otimes R(t)dt = \qquad (8)$$

$$2\int_{0}^{\infty} S(v)e^{-i2xi\tau}dv + 2\int_{0}^{\infty} S(v) \cdot F(R(t))e^{-i2xi\tau}dv =$$

$$2\int_{0}^{\infty} S(v)\{1 + F(R(t))\}e^{-i2xi\tau}dv$$

Figure 7A:
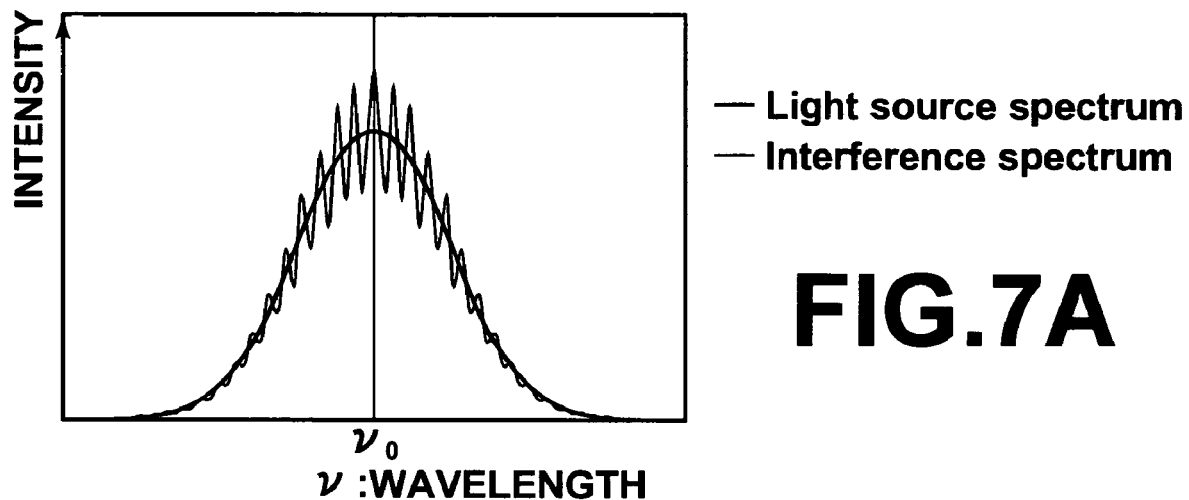
FIG. 7A is a graph showing an example of a waveform of the interference signal obtained in the optical tomography system shown in FIG. 1.
Figure 7B:
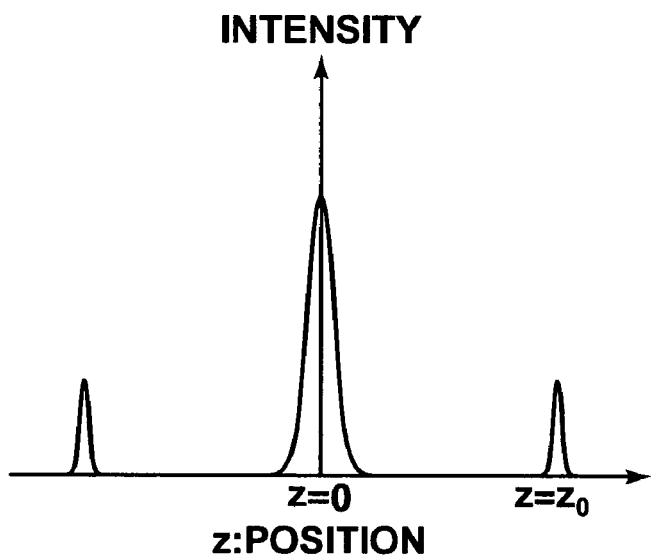
FIG. 7B is a graph showing an example of a waveform of the signal obtained by Fourier-transforming the interference signal.

In formula (8), Fourier transform of the convolutional integration is abbreviated as apparent. By this, a waveform obtained by adding the Fourier-transformed information on the reflection to the spectrum of the light source is observed as shown in FIG. 7A. By frequency-analyzing in the image obtaining means 50 the interference light beam L4 detected as shown in FIG. 7A in the interference light detecting means 140, information on the reflection in positions of depth z can be obtained as shown in FIG. 7B. The frequency analysis is effected, for instance, by Fourier-transforming the interference signal which is obtained on the basis of output of the light detecting means 144 and has a waveform such as shown in FIG. 7A. That is, by the Fourier-transform, a signal representing that an interface of reflection exists in position $z_0$ of depth as shown in FIG. 7B.

By obtaining a tomographic image by the use of spectral interference as described above, the mechanical movable part necessary to an OCT system where the optical path lengths of the reflected light beam L3 and the reference light beam L2 are changed to change the depth of measurement becomes unnecessary and the tomographic image can be rapidly obtained.

Figure 5:
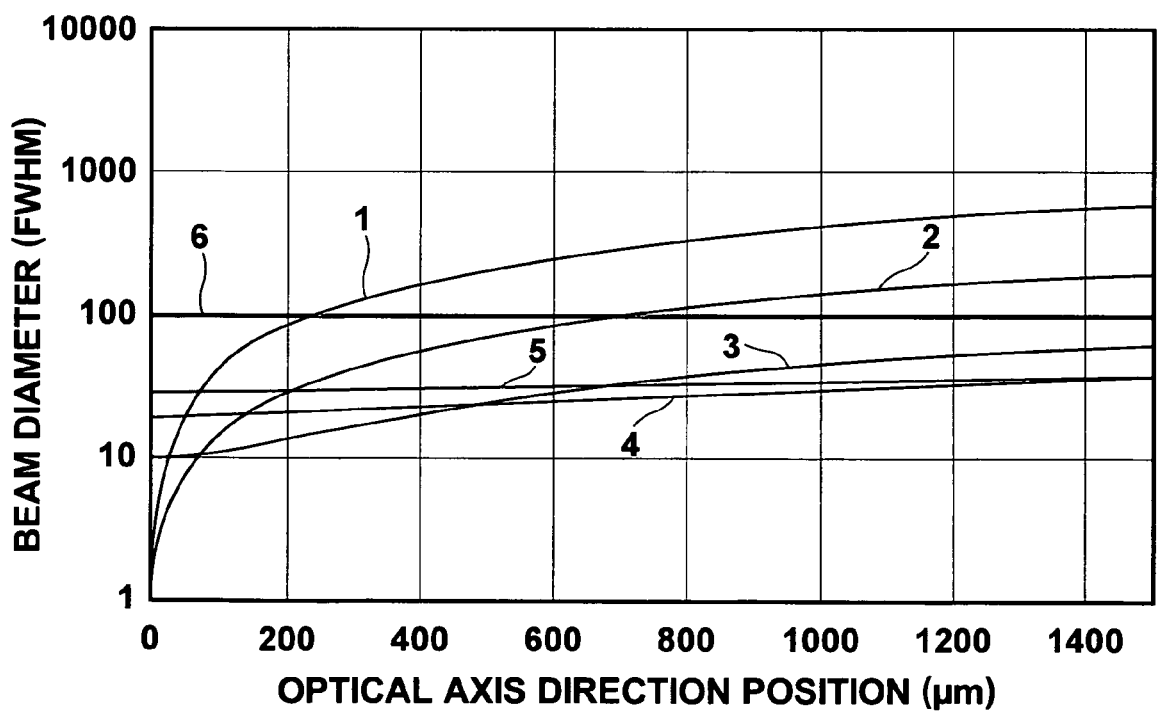
FIG. 5 is a graph showing an example of the characteristics of the change of the beam diameter with the positions in the direction of the optical axis for each beam diameter of the measuring light beam.
Figure 6:
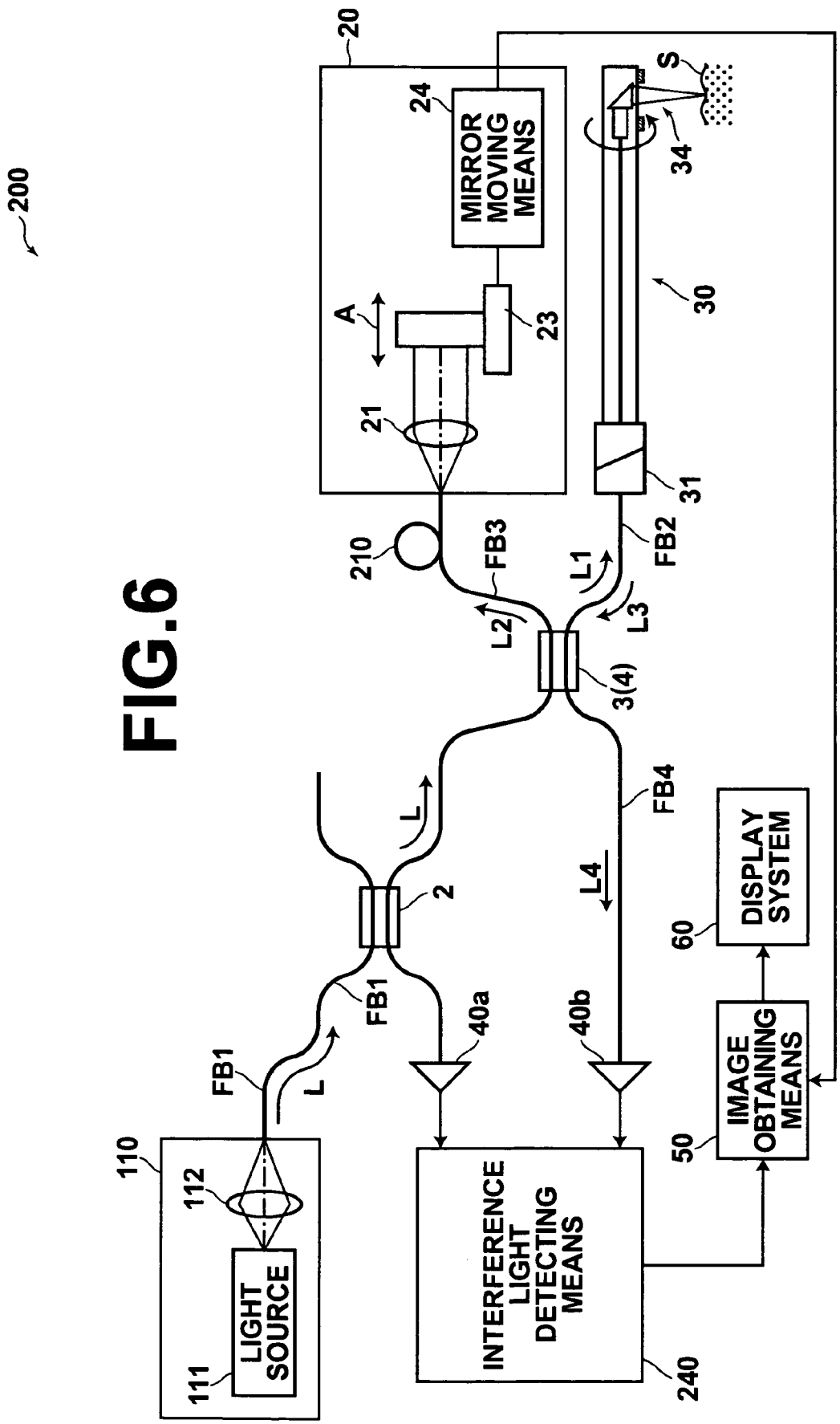
FIG. 6 is a schematic diagram showing the conventional optical tomography system.

The case of obtaining a high resolution tomographic image is to be obtained will be described next. In this case, the beam diameter Δx of the measuring light beam L1 in the converging position in the object S is set at about 5 μm, for instance, by applying a high NA collecting lens as a collecting lens 44 of a light scanning means 40. In this case, the distance in the direction of the optical axis over which Δx=5 μm is held is about 50 μm as can be understood from FIG. 5. Accordingly, there arises a problem that, when a tomographic image of an area longer than a length in the direction of the optical axis where a desired beam diameter range can be held is to be obtained while a desired lateral resolution is kept to be held, the lateral resolution deteriorates in the deeper or shallower region.

Accordingly, in this embodiment, after information on the direction of depth (A line) of a point in the object S is obtained in the manner described above, the scanning of light by the light scanning means 40 is not initiated but the reflecting mirror 22 of the optical path length adjusting means 20 is moved to change the optical path of the reference light beam L2 to a predetermined length. In this state, information on the direction of A line of the same point in the object S is obtained in the same manner as described above. The change of the optical path length of the reference light beam L2 is stepwise repeated a plurality of times and information on the direction of A line of the same point in the object S is obtained every time the optical path length of the reference light beam L2 is changed.

Figure 2A:
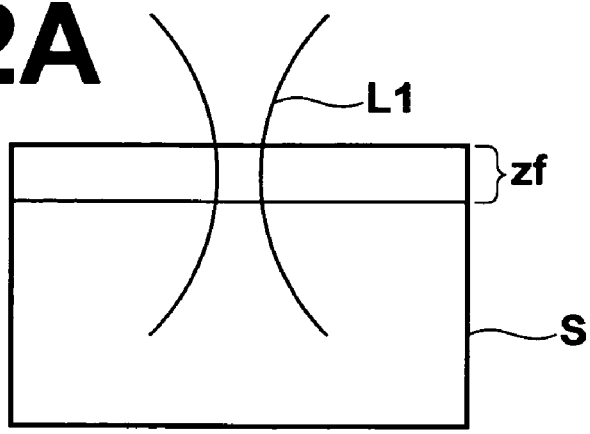
FIGS. 2A to 2C are views for illustrating the change of the focusing position of the measuring light beam in the optical tomography system shown in FIG. 1.
Figure 2B:
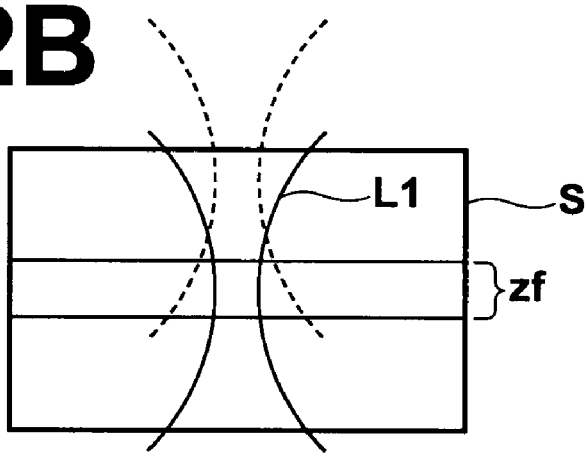
Figure 2C:
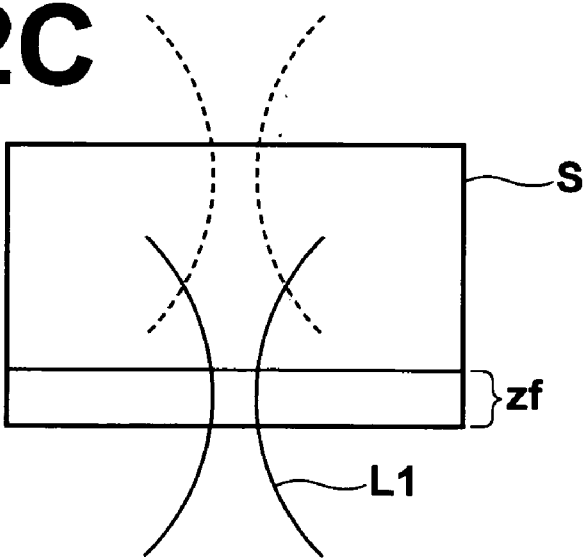
Figure 4:
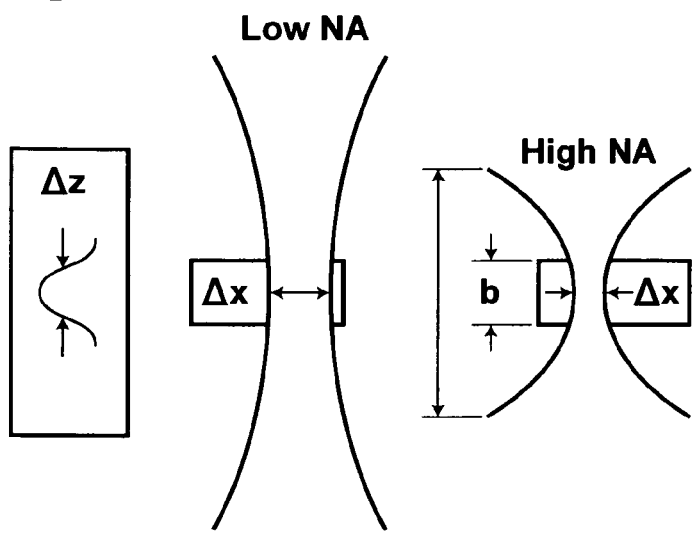
FIG. 4 is a view for illustrating the shape of the reference light beam.

As the optical path length of the reference light beam L2 is changed, the focusing range zf of the measuring light beam L1 in the object S changes in the direction of the optical axis as shown in FIGS. 2A to 2C. As the light detecting means 144 of the interference light detecting means 140, that on which a data integrated board (not shown) is mounted is employed and a plurality of pieces of above information on the direction of A line are all temporarily stored therein. When change of the optical path length of the reference light beam L2 and obtaining the A line information are repeated predetermined times for a point in the object S, position onto which the measuring light beam L1 is irradiated is changed and the same operations as described above are repeated in the position.

The image obtaining means 50 formed by a computer system reads out the plurality of pieces of the A line information from the above data integrated board, extracts data on the position in the direction of depth where the measuring light is in the focusing range out of the pieces of data read out, obtains A line information for a longer position in the direction of depth by joining a plurality of pieces of the extracted data and forms a tomographic image on the basis of the information. With this arrangement, a tomographic image high in the resolution in both the direction of the optical axis and the lateral direction can be formed.

Further, in this embodiment, since data on a plurality of positions in the direction of the optical axis can be obtained by one A line information obtaining operation, data can be obtained more rapidly than when the scanning mechanism for the measuring light beam is fed at pitches and the tomographic image can be formed in a shorter time. This point will be described more specifically, hereinbelow.

For example, when it is assumed that an area which is 3 mm in the direction of the optical axis and is 5 mm in the lateral direction is imaged at pitches in the direction of the optical axis of Δz/4=2.5 μm at a high resolution of Δx=Δz=10 μm by the conventional TD-OCT, 1,200 (3 mm/2.5 μm) points must be measured for one A line. Whereas, in the case of this embodiment, since the focal depth when Δx=10 μm is about 200 μm, only 15 (3 mm/0.2 mm) points must be measured to collect focusing A line data, whereby data can be obtained at a speed as high as 80 times the conventional system.

A second embodiment of the present invention will be described with reference to FIG. 3, hereinbelow. In FIG. 3, plan views of a light scanning means 40' and an interference light detecting means are shown in the portion a and the portion b.

The system for carrying out this method is based on a so-called bulk Michelson interferometer and the low coherence light beam L emitted from the light source 111 is divided into the measuring light beam L1 and the reference light beam L2 by a beam splitter 70 after expanded to a predetermined beam diameter by a beam expander 114. Then the reflected light beam L3, which is reflected from the object S when the measuring light beam L1 is irradiated onto the object S, and the reference light beam L2 are multiplexed by the beam splitter 70, and the interference light beam L4, thereby generated, is detected by the light detecting means.

In this embodiment, a two-dimensional spectral means 142' and a two-dimensional light detecting means 144' are employed instead of the one-dimensional spectral means 142 and the one-dimensional light detecting means 144 in the first embodiment, and collimator lenses 44' and 143' are employed instead of the collecting lenses 44 and 143 in the first embodiment. With such an arrangement, since a plurality of pieces of A line information of positions along a one-dimensional direction of the object S can be obtained altogether, the scanning of measuring light beam L1 by the light scanning means 40' has to be effected only in a one-dimensional direction.

The rapid obtainment of data in this embodiment will be described along a specific example described above in conjunction with the first embodiment. Though, in this embodiment, a plurality of pieces of lateral data (B line data) can be obtained altogether, 2,000 (5 mm/2.5 μm) points must be measured by the conventional TD-OCT. In this embodiment, since the focusing A line data can be obtained at a speed as high as 80 times the conventional system as described above, the data can be obtained at a speed as high as 1600 times the conventional system altogether. If such a rapidity can be realized, in vivo measurement on a living body while it moves becomes possible.

What is claimed is:

1. An optical tomography method in which
   low coherence light emitted from a light source is divided into measuring light and reference light,
   the measuring light is collected by a lens system to be projected onto an object of measurement,
   the reflected light from the object and the reference light are multiplexed,
   interference light of the reflected light and reference light which have been multiplexed is detected,
   intensities of the reflected light in a plurality of positions in the direction of depth of the object of measurement are detected by carrying out a Fourier analysis on each channeled spectrum obtained by decomposing the detected interference light into frequency components and
   a tomographic image of the object is obtained on the basis of the intensity of the reflected light in each position in the direction of depth, wherein the improvement comprises the steps of
   stepwise changing the optical path length of the reference light thereby adjusting the optical path length of the reference light within the focusing range with respect to the object of the measuring light collected by the lens system,
   obtaining a plurality of pieces of data representing the intensity of the reflected light in a plurality of positions in the direction of depth each time the position of the focusing range changes,
   extracting data on the position in the direction of depth where the measuring light is in the focusing range out of the pieces of data representing the intensity of the reflected light, and
   obtaining a tomographic image on the basis of the extracted piece of data.

2. An optical tomography method as defined in claim 1 in which stepwise changing the optical path length of the reference light is effected at pitches where the focusing range of the measuring light in the object changes by substantially the same extent as the focusing range of the measuring light.

3. The optical tomography method as defined in claim 1, wherein the stepwise changing comprises:
   refraining from changing the optical path length of the measuring light by a mechanical movement.

4. The optical tomography method as defined in claim 1, wherein the stepwise changing comprises:
   stepwise changing the optical path length of the reference light each time a position of a focusing range of the measuring range changes.

5. The optical tomography method as defined in claim 1, wherein the stepwise changing comprises:
   stepwise changing the optical path length of the reference light only when a position of a focusing range of the measuring range changes.

6. The optical tomography method as defined in claim 5, further comprising:
   preventing obtaining the data at unnecessarily fine pitches to increase a speed of forming the tomographic image.

7. The optical tomography method as defined in claim 2, wherein the optical path length of the reference light is stepwise changed when a diameter of a beam of the measuring light in a converging position changes with a change of a position in a direction of the optical axis to minimize a number of collected points.

8. The optical tomography method as defined in claim 7, wherein the light beam diameter is equal to approximately at least one of 10 μm, 20 μm, 30 μm and 100 μm.

9. The optical tomography method as defined in claim 8, wherein the light beam is equal to approximately 10 μm and wherein the optical path length of the reference light is stepwise changed approximately every 200 μm.

10. The optical tomography method as defined in claim 8, wherein the light beam diameter is equal to approximately 20 μm and wherein the optical path length of the reference light is stepwise changed approximately every 750 μm.

11. A spectral domain optical coherence tomography (SD-OCT) apparatus for performing the method of claim 1.

* * * * *